United States Patent
Kilemnik (10) Patent No.: US 12,409,023 B2
(45) Date of Patent: *Sep. 9, 2025

(54) URETHRAL IMPLANT

(71) Applicant: Medi-Tate Ltd., Hadera (IL)

(72) Inventor: Ido Kilemnik, Haniel (IL)

(73) Assignee: MEDI-TATE LTD., Hadera (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/257,784

(22) PCT Filed: Jul. 1, 2019

(86) PCT No.: PCT/IL2019/050727
§ 371 (c)(1),
(2) Date: Jan. 4, 2021

(87) PCT Pub. No.: WO2020/008455
PCT Pub. Date: Jan. 9, 2020

(65) Prior Publication Data
US 2022/0133462 A1    May 5, 2022

Related U.S. Application Data

(60) Provisional application No. 62/692,792, filed on Jul. 1, 2018.

(51) Int. Cl.
*A61F 2/04* (2013.01)
*A61F 2/86* (2013.01)

(52) U.S. Cl.
CPC .................. *A61F 2/04* (2013.01); *A61F 2/86* (2013.01); *A61F 2002/047* (2013.01)

(58) Field of Classification Search
CPC ......... A61F 2/04; A61F 2/86; A61F 2002/047
See application file for complete search history.

(56) References Cited

U.S. PATENT DOCUMENTS

| 5,209,725 A | 5/1993 | Roth |
| 5,499,994 A | 3/1996 | Tihon et al. |

(Continued)

FOREIGN PATENT DOCUMENTS

| EP | 3167845 A1 | 5/2017 |
| WO | 2006/040767 A1 | 4/2006 |

OTHER PUBLICATIONS

European Search Report for EP Application No. 19831066.6. (May 6, 2022).

(Continued)

*Primary Examiner* — Dinah Baria
(74) *Attorney, Agent, or Firm* — Merchant & Gould P.C.

(57) ABSTRACT

A urethral-implant is configured to be implanted within a restricted location of a urethra. The urethral-implant forms at least one closed-shape by coiling ends of a single wire section on each other. The closed-shape includes a distal section, a proximal section and two lateral sections extending between the proximal section and the distal section. The closed-shape exhibits an expanded configuration and is foldable into a compressed configuration. The urethral-implant further is configured to extend from the compressed configuration to the expanded configuration so that the distance between wire sections increases, relative to the distance between wire sections in the compressed configuration. The urethral-implant applies continuous pressure on surrounding tissue thereby applying continuous radial pressure on at least one of a urethral wall and tissue surrounding the urethral wall. The radial pressure is sufficient to cause either a widening effect, extending a urinal passage or inducing infarction.

3 Claims, 8 Drawing Sheets

(56) References Cited

U.S. PATENT DOCUMENTS

| | | |
|---|---|---|
| 8,585,730 B2 | 11/2013 | Eaton et al. |
| 2005/0015111 A1* | 1/2005 | McGuckin, Jr. ........ A61F 2/012 |
| | | 606/200 |
| 2009/0069828 A1* | 3/2009 | Martin ................ A61B 17/221 |
| | | 606/159 |
| 2011/0276081 A1 | 11/2011 | Kilemnik |
| 2016/0317180 A1 | 11/2016 | Kilemnik |
| 2017/0000598 A1 | 1/2017 | Bachar |
| 2017/0135830 A1 | 5/2017 | Harkin et al. |

OTHER PUBLICATIONS

International Search Report and Written Opinion for PCT/IL2019/050727, mailed Oct. 29, 2019.

* cited by examiner

URETHRAL IMPLANT

This application is a National Stage application of PCT/IL2019/05727, filed Jul. 1, 2019, which claims priority to U.S. Provisional Patent Application No. 62/692,792 filed Jul. 1, 2018 which applications are incorporated herein by reference. To the extent appropriate, a claim of priority is made to each of the above-disclosed applications.

FIELD OF THE DISCLOSED TECHNIQUE

The disclosed technique relates to implants, in general, and to urethral implants produced from a single wire section, in particular.

BACKGROUND OF THE DISCLOSED TECHNIQUE

The urethra is the tube that carries the urine from the bladder to the external urethral orifice, to remove the urine from the body. In some cases, the urethra may be partially or fully blocked due to conditions such as prostate enlargement or urethral stricture, resulting in conditions such as Benign Prostatic Hyperplasia (BPH), prostatic Bladder Neck Obstruction (BNO) and the like, and the flow of fluids in the urethra is restricted and even blocked. Such a partial or full block of the urethra may cause discomfort and pain and may even result in infections.

Transurethral incision of the prostate (TUIP) is an endoscopic procedure usually performed under general anaesthetic in which a surgeon employs an instrument (e.g., a scalpel, a laser beam generator and an electrical current actuator) inserted into the urethra for making incisions in the bladder neck where the prostate meets the bladder (i.e., more specifically in the midline to the level of the verumontanum). Incising the muscles in the bladder neck area relieves the obstructive effect of the prostate on the bladder neck and prostatic urethra and relaxes the opening of the bladder, thus decreasing resistance to the flow of urine out of the bladder. It is noted that, no tissue is removed during TUIP.

Infarction is a process resulting in a macroscopic area of necrotic tissue in some organ caused by loss of adequate blood supply. The inadequate blood supply can result from pressure applied to the blood vessels. Even by applying a relative small but continuous pressure on a tissue, one can block the tiny blood vessels within the tissue and induce infarction.

Known in the art are implants which are inserted through the urethral orifice, in a compressed state to the blocked section of the urethra. When positioned in the blocked section of the urethra, the implant expands and widens the blocked section thus enabling the flow of fluids through the urethra. PCT Patent Application Publication WO 2006/040767 A1, to Kilemnik, and entitled "Prostate Treatment Stent" is directed at a tissue dissecting implant. The implant is spring-shaped and includes a plurality of rings elastically coupled there-between. Adjacent rings apply pressure on tissues caught between the rings, thereby pinching the caught tissues and inducing necrosis.

US Patent Application Publication No. 2011/0276081 to Kilemnik, and entitled "Radial Cutter Implant" is directed at an implant for applying radial forces on the tissues surrounding it. The implant includes wires for applying radial pressure on the surrounding tissues. Each of the wires extends in a different radial direction, and therefore, each wire applies pressure on different tissues. The implant can further include a longitudinal central tube, such that the wires are coupled with a proximal end and a distal end of the tube. The tube supports the wires and provides structural stability to the implant. The distal end of the wires is positioned within the bladder of the subject, and may irritate the bladder.

U.S. Pat. No. 5,209,725 issued to Roth, and entitled "Prostatic Urethra Dilatation Catheter System and Method", is directed to an instrument for performing a transurethral balloon dilatation procedure of the prostate. The balloon dilatation instrument includes a hollow catheter and optical viewing means. The hollow catheter includes a shaft, an inflatable optically transparent balloon, and at least one suitable visible marking. The distal end portion of the shaft is made of an optically transparent material. The inflatable optically transparent balloon is coupled with the distal end portion of the shaft, and is sized to dilate the prostatic urethra. The at least one suitable visible marking is positioned on the catheter proximally to the balloon, such that the marking can be visualized relative to a predetermined anatomical landmark (e.g., verumon tanum). In this manner, proper positioning of the balloon, relative to the prostatic urethra, is performed prior to and during the dilation of the prostatic urethra. The optical viewing means is slidable within the catheter, for visibly viewing the marking intraluminally from within the catheter. The balloon is correctly located relative to the prostatic urethra. The balloon is inflated so as to dilate the prostatic urethra without damaging the external sphincter at the apex of the prostate.

U.S. Pat. No. 5,499,994 issued to Tihon et al., and entitled "Dilation Device for the Urethra", is directed to a dilation device for opening a portion of an obstructed urethra. The dilation device includes an inner hollow tubular core and an outer confining covering. The inner hollow tubular core defines a lumen therein. The lumen is a conduit of sufficient diameter to permit urine to flow freely there-through from the bladder. The core is substantially non-collapsible. The outer confining covering is capable of expanding radially outwardly to a predetermined extent. The covering has a length of at least partially that of the obstructed portion of the urethra. The dilation device can further include retractable spikes for anchoring the device in its intended position.

SUMMARY OF THE PRESENT DISCLOSED TECHNIQUE

A urethral implant configured to be implanted within a restricted location of a urethra. The urethral implant, forms at least one closed shape by coiling ends of the single wire section on each other. The at least one closed shape includes a distal section, a proximal section and two longitudinal sections extending between the proximal section and the distal section. The at least one closed shape exhibits an expanded configuration and is foldable into a compressed configuration. The urethral implant further being configured to extend from the compressed configuration to the expanded configuration such that the distance between sections of the wire increases, relative to the distance between the sections of the wire in the compressed configuration. The urethral implant being for applying continuous pressure on surrounding tissue, thereby applying continuous radial pressure on at least one of a urethral wall and tissue surrounding the urethral wall in the restricted location. The radial pressure being sufficient to cause at least one of, a widening effect, extending a urinal passage, and inducing infarction.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a urethral implant for applying continuous pressure on the surrounding tissue, thereby causing ischemia, which results in necrosis. The urethral implant is made of a single wire section, forming at least one closed shape which includes a distal section, a proximal section and two longitudinal sections extending between the proximal section and the distal section. The closed shape exhibits an expanded configuration and is foldable into a compressed configuration. The urethral implant is further configured to extend from the compressed configuration to the expanded configuration such that the distance between sections of said wire increases, relative to the distance between these sections in the compressed configuration. The urethral is configured to be implanted within urethra. For example, the urethral implant may be implanted at a urethral stricture location, for applying pressure on the surrounding tissue (i.e., the inner wall) of the urethra, thereby causing ischemia at the stricture location, which results in necrosis and the widening of the urethra, allowing fluid to flow through the urethra. The urethral implant may include at least two closed shapes where each closed shape has a proximal section, a distal section and two longitudinal sections extending between the respective proximal section and the distal section. Adjacent pairs of the at least two closed shapes share at least one common longitudinal section.

Figure 1:
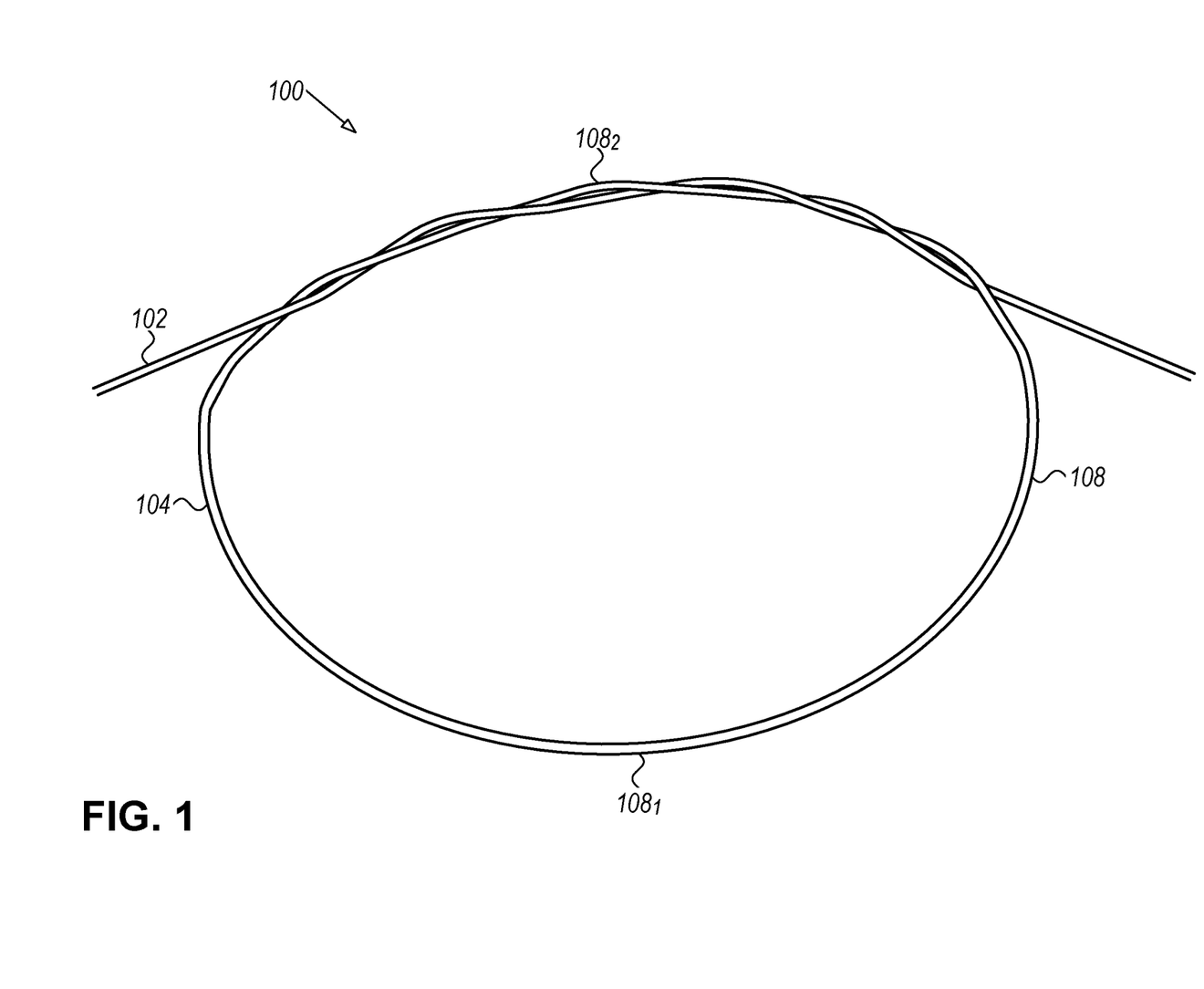
FIG. 1 is a schematic illustration of a urethral implant, constructed and operative in accordance with an embodiment of the disclosed technique.

Reference is now made to FIG. 1, which is a schematic illustration of a urethral implant, generally referenced 100, constructed and operative in accordance with an embodiment of the disclosed technique. Urethral implant 100 is made of a single wire section 102, forming a closed shape, which includes a distal section 104, a proximal section 106 and two longitudinal sections $108_1$ and $108_2$ extending between distal section 104 and the proximal section 106. Urethral implant 100 is formed by creating the closed shape with wire 102 and then coiling wire 102 on itself.

Figure 2:
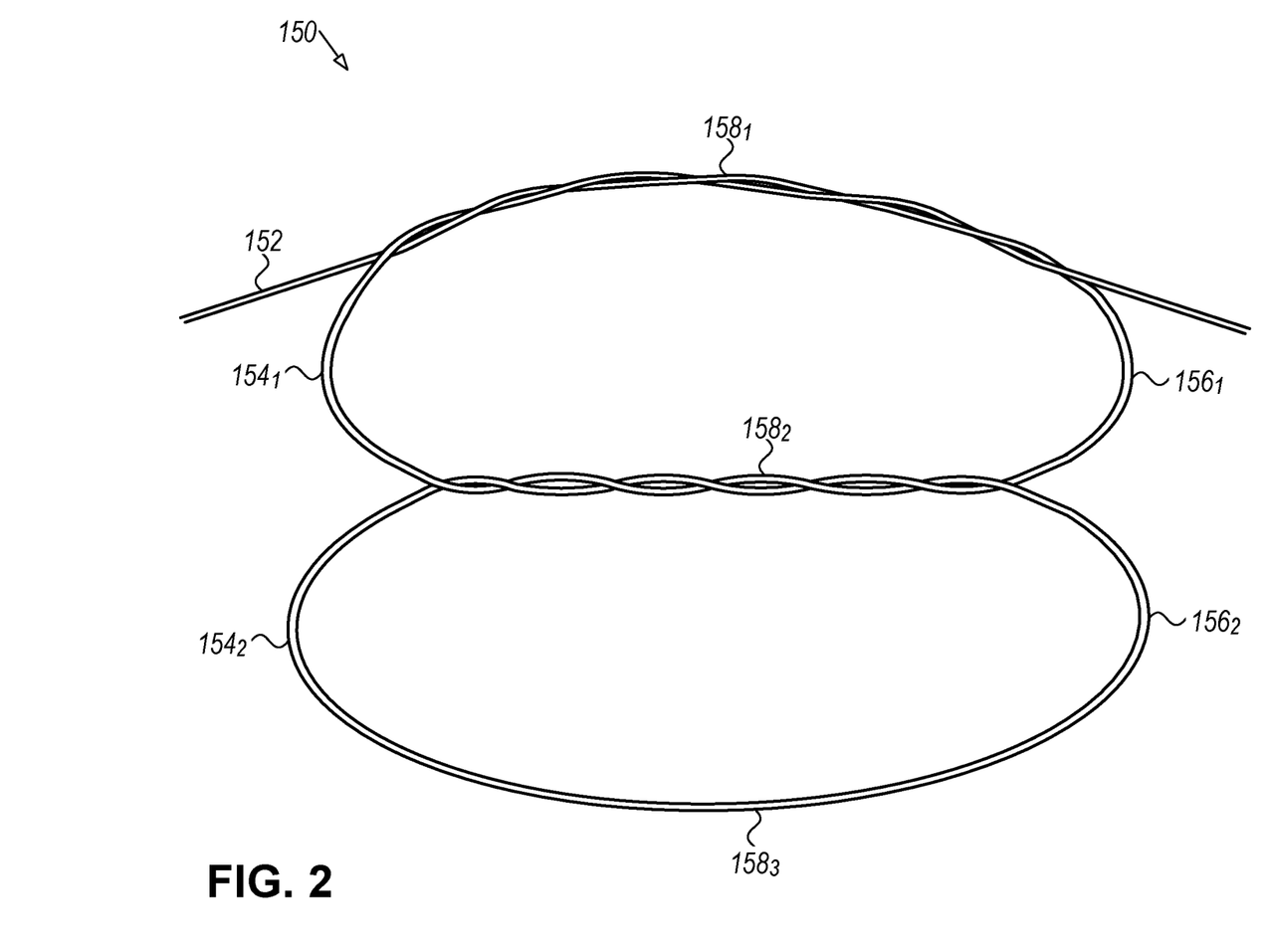
FIG. 2 is a schematic illustration of a urethral implant, constructed and operative in accordance with another embodiment of the disclosed technique.

Reference is now made to FIG. 2, which is a schematic illustration of a urethral implant, generally referenced 150, constructed and operative in accordance with another embodiment of the disclosed technique. Urethral implant 150 is made of a single wire section 152, forming two closed shapes. The first closed shape includes a distal section $154_1$, a proximal section $156_1$ and two longitudinal sections $158_1$ and $158_2$ extending between distal section $154_1$ and the proximal section $156_1$. The second closed shape includes a distal section $154_2$, a proximal section $156_2$ and two lateral longitudinal sections $158_2$ and $158_3$ extending between distal section $154_2$ and the proximal section $156_2$. Lateral Longitudinal section $158_2$ is a common lateral section between the two closed shapes. Urethral implant 150 is formed by first creating the first closed shape with wire 152 and then coiling wire 152 on itself. Coiling wire 152 on itself creates two wire end extensions of wires section 152. Then, the second closed shape is formed from the two wire end extensions of wire 152 and coiling the two wire end extensions of wire 152 one with the other.

Figure 3:
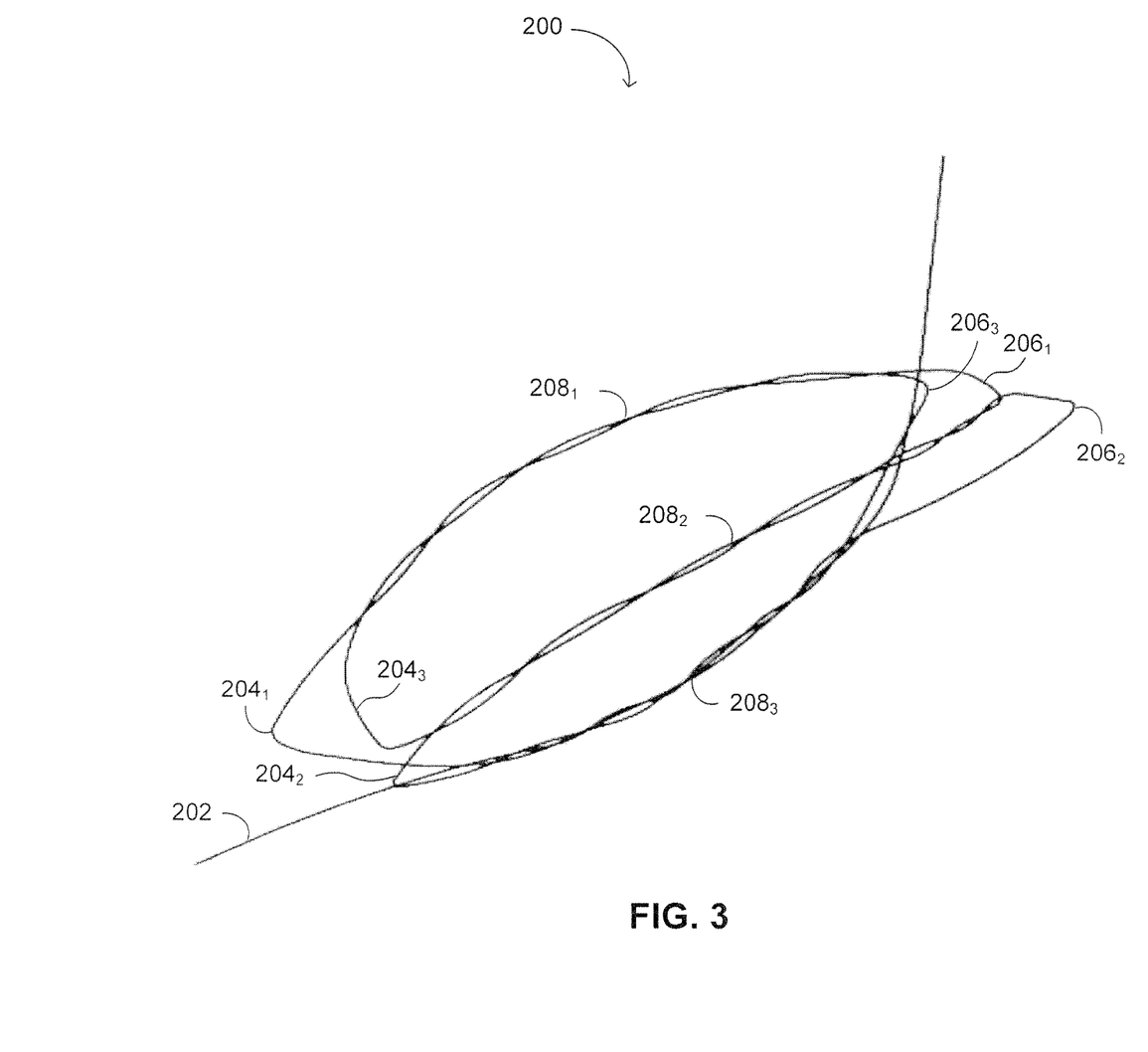
FIG. 3 is a schematic illustration of a urethral implant, constructed and operative in accordance with a further embodiment of the disclosed technique.

Reference is now made to FIG. 3, which is a schematic illustration of a urethral implant, generally referenced 200, constructed and operative in accordance with a further embodiment of the disclosed technique. Urethral implant 200 is made of a single wire 202, forming three closed shapes. The first closed shape includes a distal section $204_1$, a proximal section $206_1$ and two longitudinal sections $208_1$ and $208_2$ extending between distal section $204_1$ and the proximal section $206_1$. The second closed shape includes a distal section $204_2$, a proximal section $206_2$ and two lateral longitudinal sections $208_2$ and $208_3$ extending between distal section $204_2$ and the proximal section $206_2$. The third closed shape includes a distal section $204_3$, a proximal section $206_3$ and two lateral longitudinal sections $208_3$ and $208_1$ extending between distal section $204_3$ and the proximal section $206_3$. Thus, lateral longitudinal section $208_1$ is common to the first and the third closed shapes. Thus, lateral longitudinal section $208_2$ is common to the first and the second closed shapes and lateral longitudinal section $208_2$ $208_3$ is common to the second and the third closed shapes.

Urethral implant 200 is formed by first creating the first closed shape wire 202 and then coiling wire 202 on itself forming longitudinal sections $208_1$ and $208_2$ similar to as described above in conjunction with FIG. 1. Then, the second closed shape is formed with the wire end extensions of wire 202 and coiling the two extensions of wire 202 one with the other, similar to as described above in conjunction with FIG. 2, thus forming longitudinal section $208_3$. The third closed shape is formed with the two wire end extensions of wire 202, by coiling the two wire end extension of wire 202 on longitudinal section $208_1$.

Figure 4:
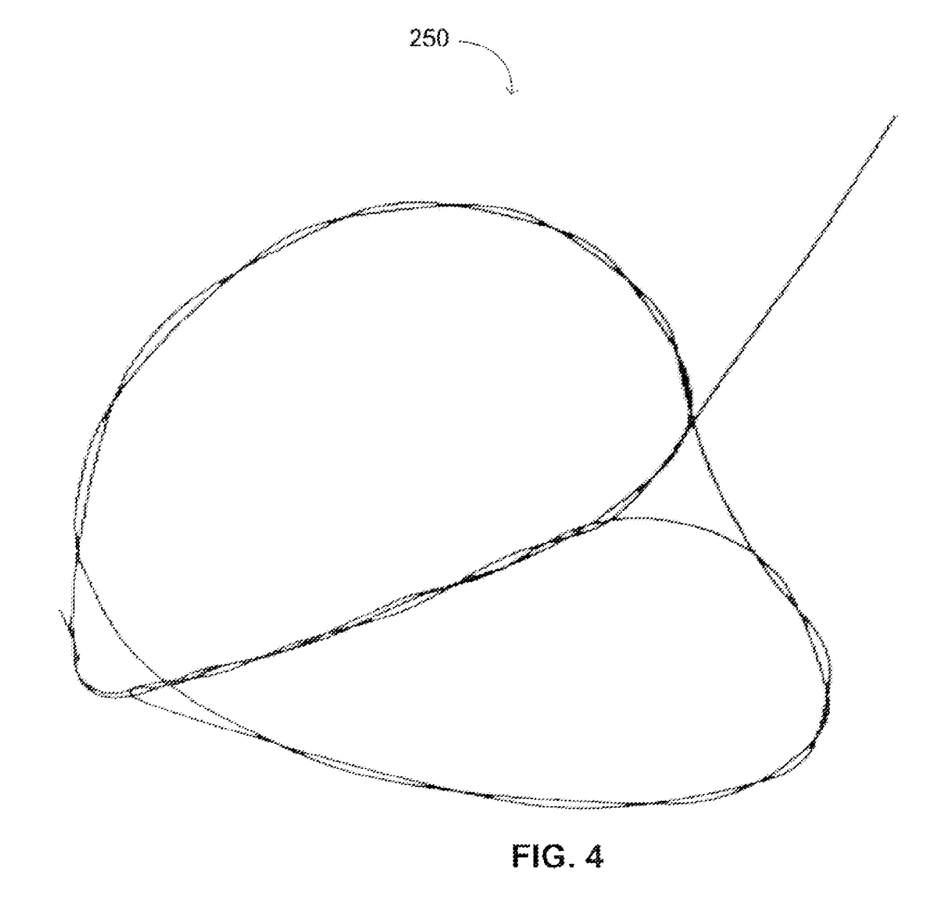
FIG. 4 is a schematic illustration of a urethral implant, constructed and operative in accordance with another embodiment of the disclosed technique.

Reference is now made to FIG. 4, which is a schematic illustration of a urethral implant, generally referenced 250, constructed and operative in accordance with another embodiment of the disclosed technique. Urethral implant 250 is similar in construction form and functionality to urethral implant 200 (FIG. 3).

Each of the single wire urethral implants 100, 150, 200 and 250 described hereinabove is made from materials such as stainless steel or Shape Memory Alloy (SMA), such as Nickel Titanium alloy (Nitinol). The transition between the compressed configuration to the expanded configuration occurs due to the elastic (i.e., spring like) characteristics of the material. Each of the single wire urethral implants 100, 150, 200 and 250 described hereinabove may be wider at the proximal end than at the distal end thereof for preventing said removable implant from moving in the distal direction. Alternatively, each of the single wire urethral implants 100, 150, 200 and 250 described hereinabove may be wider at the distal end than at the proximal end thereof for preventing said removable implant from moving in the proximal direction. According to yet another alternative, each of the single wire urethral implants 100, 150, 200 and 250 described hereinabove may be narrower at the middle thereof than at the distal and proximal portions thereof, for preventing said removable implant from moving in the proximal direction and in the distal direction. According to yet another alternative, each of the single wire urethral implants 100, 150, 200 and 250 described hereinabove may exhibit the shape of a butterfly wing.

Figure 5A:
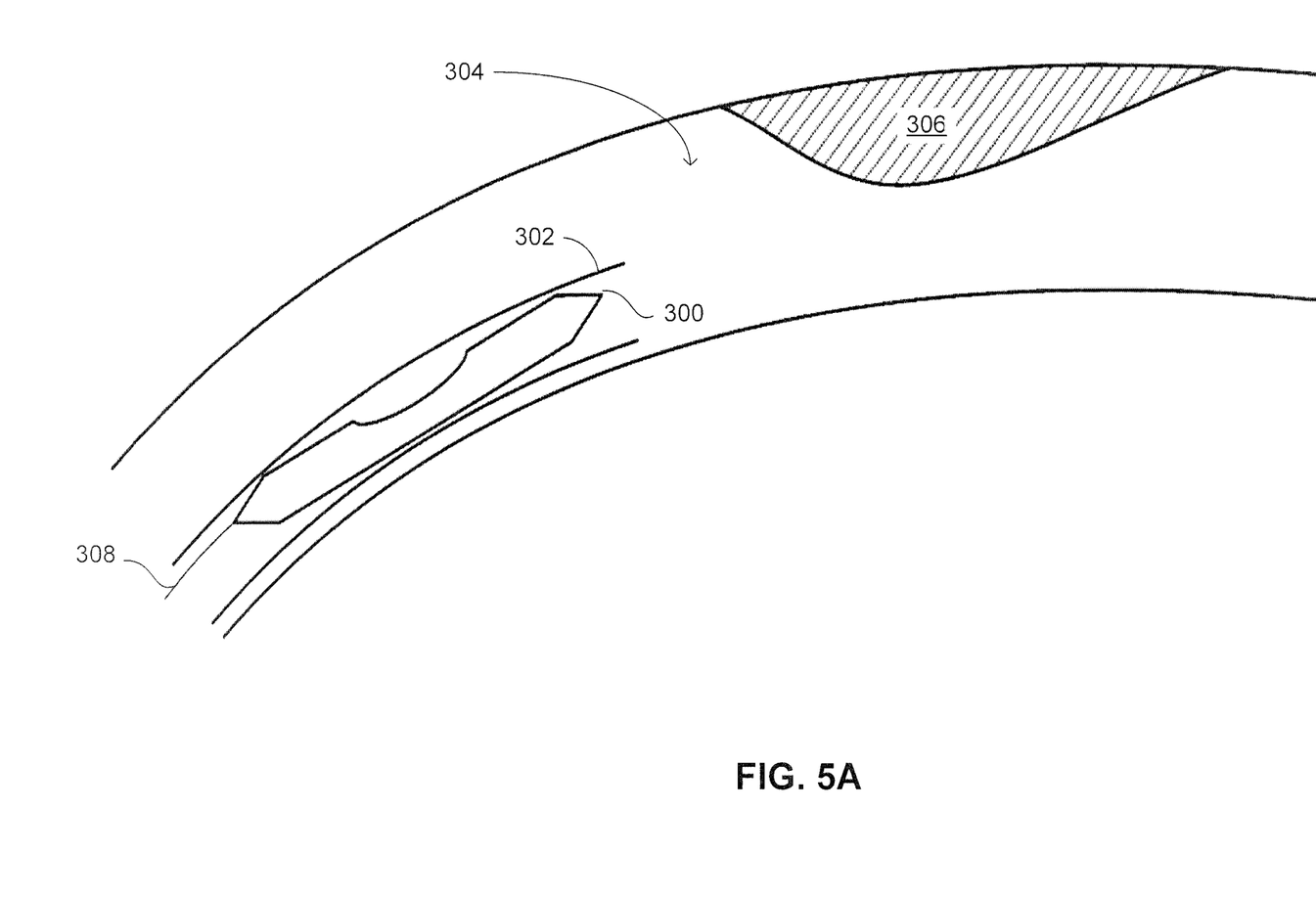
FIGS. 5A-5C are schematic illustrations of deployment of a urethral, operative in accordance with a further embodiment of the disclosed technique.
Figure 5B:
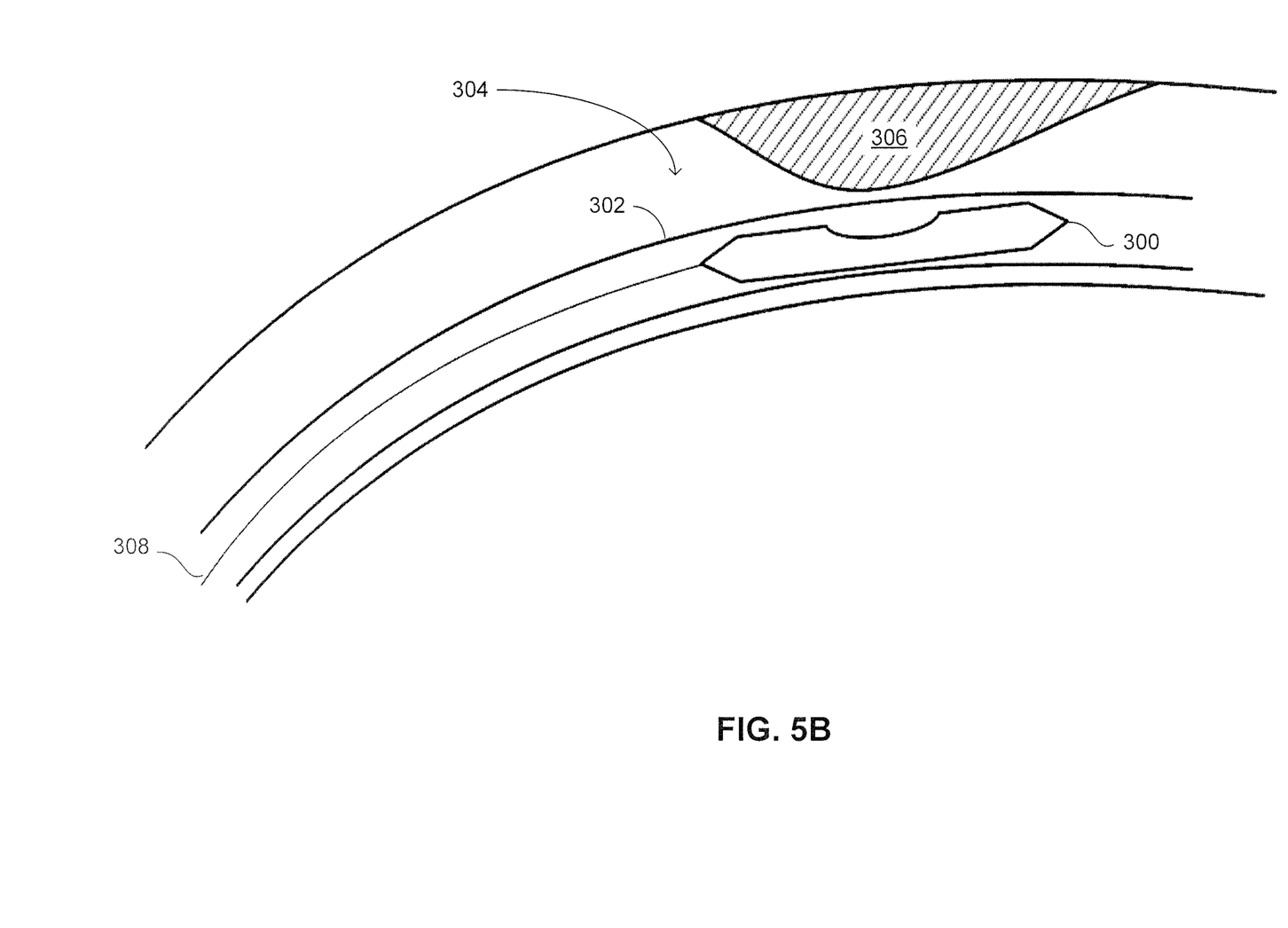
Figure 5C:
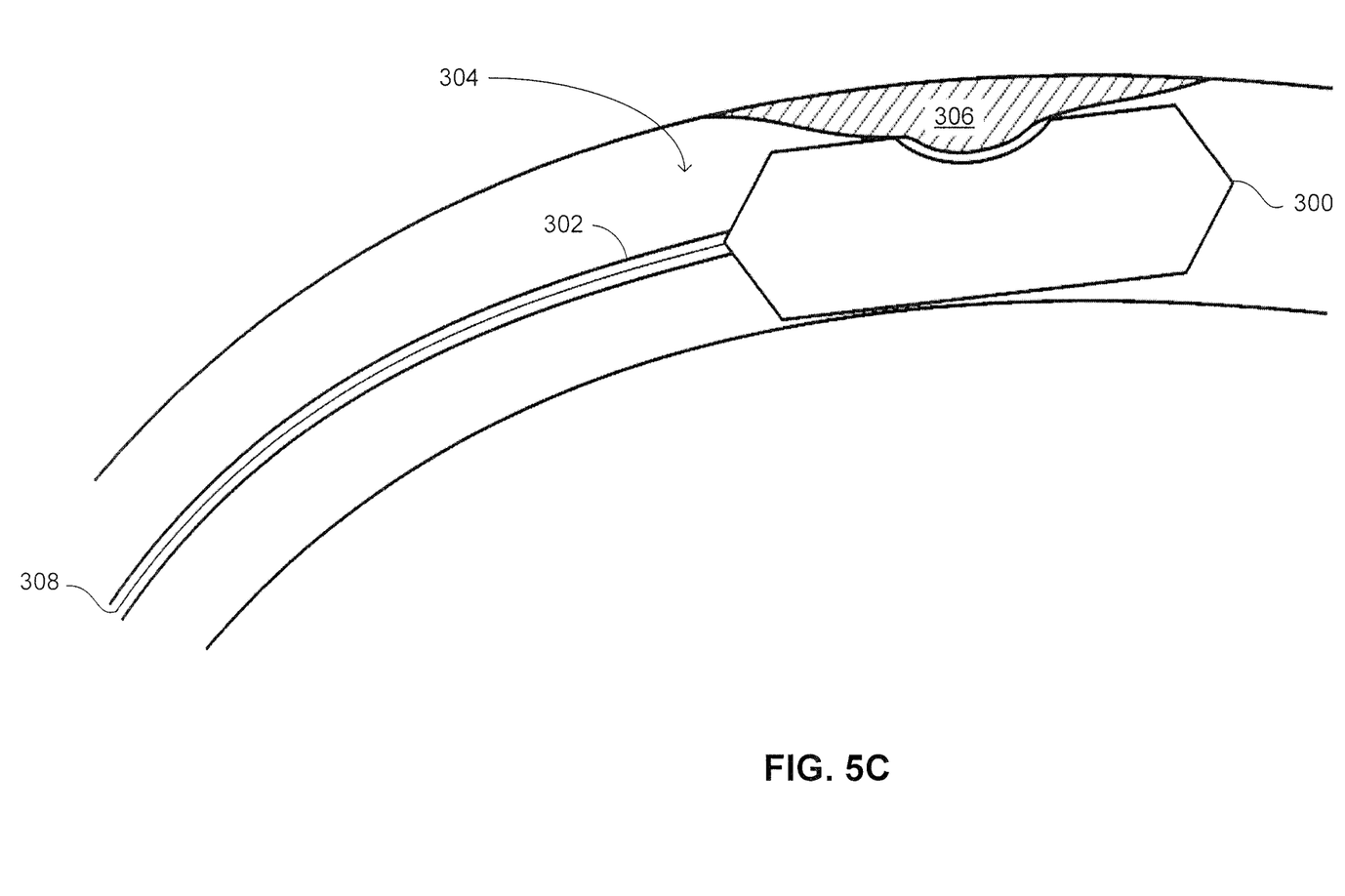

Reference is now made to FIGS. 5A-5C which are schematic illustrations of deployment of a urethral implant 300, operative in accordance with a further embodiment of the disclosed technique. Initially, urethral implant is in a compressed configuration and is located within an overtube 302 also referred to as a restrainer. Overtube 302, with urethral implant 300 compressed therein is inserted into the urethra 304, until urethral implant 300 is aligned (FIG. 5B) with a stricture 306. Thereafter, overtube 302 is pulled over urethral implant 300. Once overtube 302 is removed from over urethral implant 300, urethral implant 300 expands to the expanded configuration thereof (FIG. 5C). As urethral implant extends from the compressed configuration to the expanded configuration, urethral implant 300 applies a force on stricture 306. As a result, urethral implant 300 applies pressure on the necrosis or scar tissue at stricture 306 thereby dissecting the necrosis or scar tissue and widening urethra 304 at the stricture location. After the treatment, the implant may be pulled out of urethra 304 by reinserting overtube 302 and pulling on lead wire 308 to reinsert urethral 304 into over tube 302. Over tube 302 is then pulled out of urethra. Alternatively, urethral implant 300 may be pulled out of urethra 304 directly by pulling on lead wire 308 (i.e., without reinserting overtube 302).

In FIGS. 5A-5C, urethral implant 300 includes a concave portion in at least one of the longitudinal sections thereof. In the expanded configuration, tissue fills this concave portion, thereby anchoring urethral implant in position.

The exemplary urethral implants described hereinabove are made of a single wire and exhibit a "closed loop configuration". In a "closed loop configuration", all the longitudinal sections are connected to both the proximal and the distal sections. However, the urethral implants according to the disclosed technique may also exhibit an "open loop configuration", where at least one of the longitudinal sections is connected only to the proximal section or only to the distal section. Also, the urethral implants according to the disclosed technique may be cut out of a metal sheet or tube.

Figures 6A, 6B, 7A:
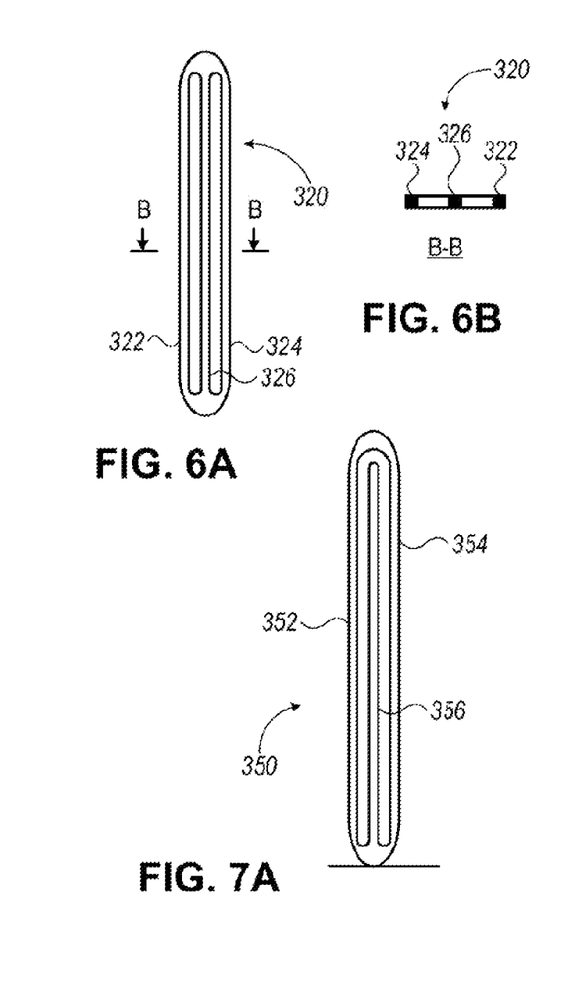
FIGS. 6A-6E are schematic illustrations of a urethral implant, constructed and operative in accordance with another embodiment of the disclosed technique.
FIGS. 7A-7C are schematic illustrations of a urethral implant, constructed and operative in accordance with another embodiment of the disclosed technique.
Figures 6C, 6D, 6E:
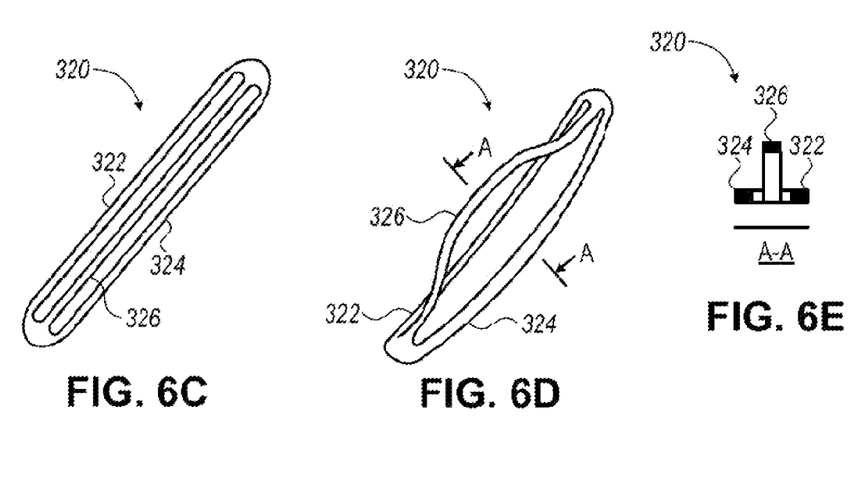

Reference is now made to FIGS. 6A-6E, which are schematic illustrations of a urethral implant, generally referenced 320, constructed and operative in accordance with another embodiment of the disclosed technique. Urethral implant 320 includes three longitudinal sections 322, 324 and 326 arranged in a closed loop configuration (i.e., longitudinal sections 322, 324 and 326 are connected to proximal section and the distal section of urethral implant 320). Urethral implant 320 is cut out from a metal sheet or tube. FIG. 6A depicts a top view of urethral implant 320 in a compressed configuration. FIG. 6B, depicts cross-section B-B of urethral implant 320 where longitudinal sections 322, 324 and 326 (as shown) are coplanar, in the compressed configuration. FIG. 6C depicts an isometric view of urethral implant 320 in a compressed configuration. FIG. 6D depicts an isometric view of urethral implant 320 in an expanded configuration. FIG. 6E, depicts cross-section A-A of urethral implant 320 in the expanded configuration.

Figure 7B:
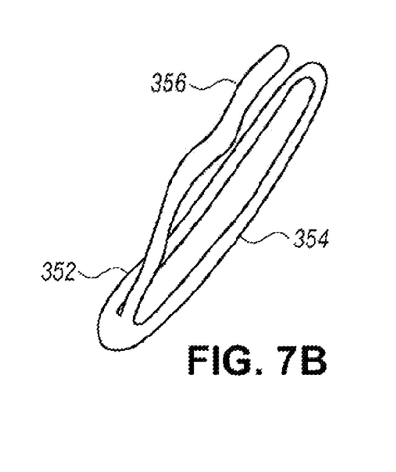
Figure 7C:
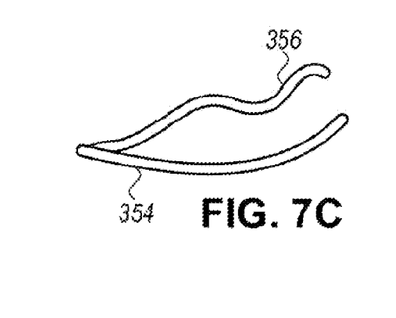

Reference is now made to FIGS. 7A-7C, which are schematic illustrations of a urethral implant, generally referenced 350, constructed and operative in accordance with a further embodiment of the disclosed technique. Urethral implant 350 includes three longitudinal sections 352, 354 and 356 arranged in an open loop configuration (i.e., where at least one of the longitudinal sections is connected only to the proximal section or only to the distal section). Urethral implant 350, includes longitudinal section 356 that is connected only to the proximal section. Urethral implant 350 is also cut out from a metal sheet or tube. FIG. 7A depicts a top view of urethral implant 350 in a compressed configuration. FIG. 7B depicts an isometric view of urethral implant 350 in an expanded configuration. FIG. 7C depicts a side view of urethral implant 350 in the expanded configuration.

It will be appreciated by persons skilled in the art that the disclosed technique is not limited to what has been particularly shown and described hereinabove. Rather the scope of the disclosed technique is defined only by the claims, which follow.

The invention claimed is:

1. A urethral implant configured for implantation within a restricted location of a urethra, said urethral implant is made of a sheet material having at least one cutout, and formed from three longitudinal sections that extend between a distal section and a proximal section of said urethral implant, said urethral implant is flexible between: a compressed configuration that enables deployment of said urethral implant to said restricted location; and an expanded configuration that enables said urethral implant to apply continuous pressure on said restricted location, thereby extending said restricted location of said urethra, wherein said three longitudinal sections of said urethral implant are coplanar in said compressed configuration, and non-coplanar in said expanded configuration.

2. The urethral implant according to claim 1, wherein at least one longitudinal section of said three longitudinal sections is connected to one of said distal section or said proximal section.

3. The urethral implant according to claim 1, wherein said urethral implant is cutout from a metal material.

* * * * *